(12) United States Patent
Medaer et al.

(10) Patent No.: US 7,317,115 B2
(45) Date of Patent: Jan. 8, 2008

(54) MANDELATES SALTS OF SUBSTITUTED TETRACYCLIC TETRAHYDROFURAN DERIVATIVES

(75) Inventors: Bart Petrus Anna Maria Jozef Medaer, Lille (BE); Sigrid Carl Maria Stokbroekx, Beerse (BE); Yves Georges Ruysschaert, Vosselaar (BE); Joannes Josephus Maria Willems, Oud-Turnhout (BE); Johan Erwin Edmond Weerts, Beerse (BE)

(73) Assignee: Janssen Pharmaceutica, N.V. (BE)

( * ) Notice: Subject to any disclaimer, the term of this patent is extended or adjusted under 35 U.S.C. 154(b) by 182 days.

(21) Appl. No.: 10/491,799

(22) PCT Filed: Nov. 8, 2002

(86) PCT No.: PCT/EP02/11136

§ 371 (c)(1),
(2), (4) Date: Apr. 5, 2004

(87) PCT Pub. No.: WO03/040122

PCT Pub. Date: May 15, 2003

(65) Prior Publication Data

US 2005/0085533 A1   Apr. 21, 2005

(30) Foreign Application Priority Data

Nov. 9, 2001   (EP) .................................. 01204465

(51) Int. Cl.
*C07D 307/77* (2006.01)
(52) U.S. Cl. ........................................ 549/457; 514/468
(58) Field of Classification Search ................ 549/457; 514/468
See application file for complete search history.

(56) References Cited

U.S. PATENT DOCUMENTS 5,658,899 A * 8/1997 Hansen et al. ......... 514/217.02
6,667,317 B2 * 12/2003 Chenard et al. ............ 514/323

FOREIGN PATENT DOCUMENTS

| DE | 3644462 A1 | 12/1986 |
| WO | WO 97/38991 A1 | 10/1997 |
| WO | WO 97/44014 A1 | 11/1997 |
| WO | WO 99/19317 A1 | 4/1999 |

OTHER PUBLICATIONS

International Search Report dated Mar. 14, 2003 for PCT/EP02/11136.

Hoyer, Daniel et al., VII. International Union of Pharmacology Classification of Receptors for 5-Hydroxytryptamine (Serotonin), Pharmacological Reviews, The American Society for Pharmacology and Experimental Therapeutics, 1994, vol. 46, No. 2, pp. 157-203.
Meert, Theo F., et al., "Partial and Complete Blockade of 5-Hydroxytryptophan (5-HTP)-induced Head Twitches in the Rat: A Study of Ritanserin (R 55 667), Risperidone (R 64 766), and Related Compounds," Drug Development Research, 13: 237-244 (1988).
Niemegeers, C.J.E. et al., "Interaction of Drugs with Apomorphine, Tryptamine and Norepinephrine. A New In vivo Approach: the ATN-Test in Rats," Arch. Int. Pharmacodyn., 227, 238-253 (1977).
Monkovic, I. et al., "Substituted Tetrahydrofurfurylamines as Potential Antidepressants," Journale of Medicinal Chemistry (1973), vol. 16, No. 4, pp. 403-407.

* cited by examiner

Primary Examiner—Amelia A. Owens
(74) Attorney, Agent, or Firm—Woodcock Washburn LLP

(57) ABSTRACT

The object of the present invention is a novel mandelate salt of a substituted tetracyclic tetrahydrofuran derivative according to Formula (I)

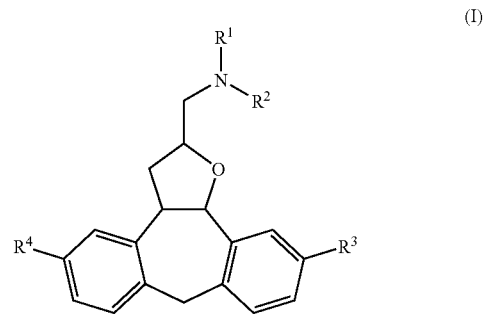

the N-oxide forms and the stereochemically isomeric forms thereof, wherein $R^1$ and $R^2$ each independently are hydrogen or $C_{1-6}$alkyl and $R^3$ and $R^4$ each independently are hydrogen or halogen. In the foregoing definitions $C_{1-6}$alkyl defines straight and branched saturated hydrocarbon radicals having from 1 to 6 carbon atoms such as, for example, methyl, ethyl, propyl, butyl, 1-methylpropyl, 1,1-dimethylethyl, pentyl or hexyl. The novel mandelate salt is not light-sensitive and is far more stable than the prior art salts at room temperature, enhanced temperature and at relative high humidities and in aqueous media. Also disclosed are pharmaceutical compositions comprising mandelate salts according to the invention, mandelate salts according to the invention for use as a medicine, a process for preparing the mandelate salts according to the invention and the use of the mandelate salts and pharmaceutical compositions comprising mandelate salts according to the invention for the treatment or the prevention of CNS disorders, cardiovascular disorders and gastrointestinal disorders.

9 Claims, 1 Drawing Sheet

Figure 1 : Adsorption/desorption behavior of various salts of Compound x.
(A=citrate ; B=malonate ; C=succinate ; D=tartrate ; E=ditoluoyltratrate ; F=mandelate)
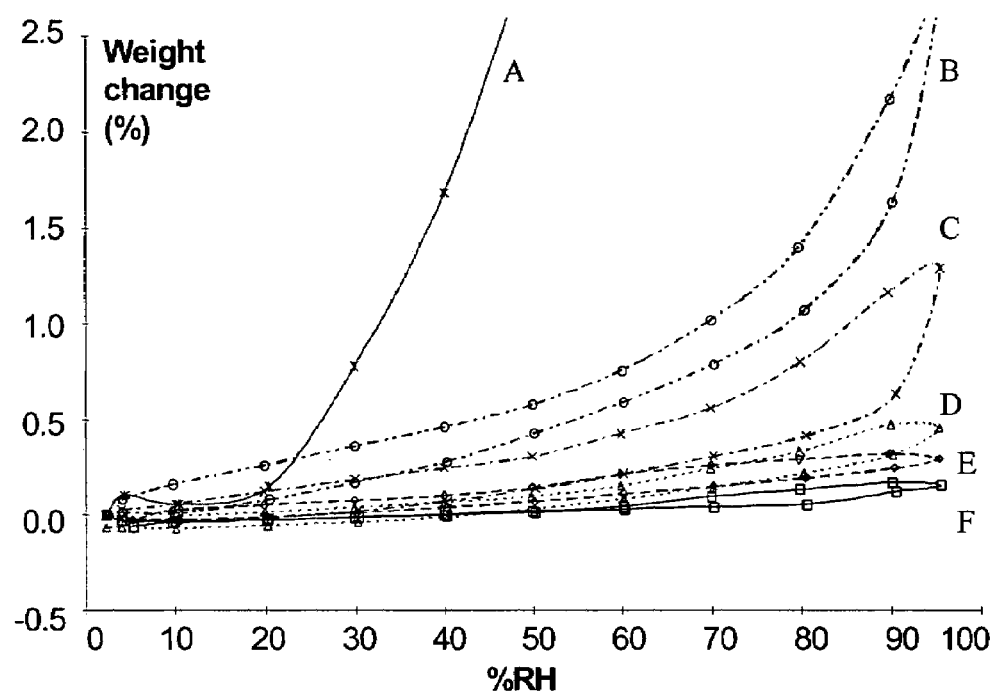

MANDELATES SALTS OF SUBSTITUTED TETRACYCLIC TETRAHYDROFURAN DERIVATIVES

CROSS REFERENCE TO RELATED APPLICATIONS

This application is the national stage of Application No. PCT/EP02/11136, filed Nov. 8, 2002, which application claims priority from EP 01204465.7 filed Nov. 9, 2001.

The present invention is concerned with novel mandelate salts of a substituted tetracyclic tetrahydrofuran derivative according to Formula (I)

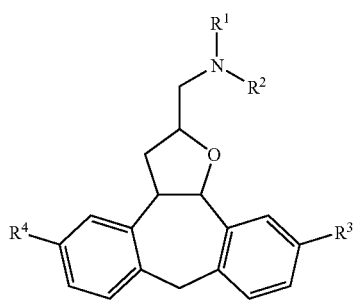

the N-oxide forms and the stereochemically isomeric forms thereof, wherein $R^1$ and $R^2$ each independently are hydrogen or $C_{1-6}$alkyl and $R^3$ and $R^4$ each independently are hydrogen or halogen, as well as pharmaceutical compositions comprising mandelate salts according to the invention, mandelate salts according to the invention for use as a medicine, a process for preparing the mandelate salts according to the invention and the use of the mandelate salts and pharmaceutical compositions comprising mandelate salts according to the invention for the treatment or the prevention of CNS disorders, cardiovascular disorders and gastrointestinal disorders.

Compounds according to Formula (I) are known from WO99/19317 and WO97/38991. Also known from said references are acid addition salts of the compounds according to Formula (I), comprising salts based on tartaric acid (D and L-forms), hydrochloric acid, hydrobromic acid and malic acid. However, the known acid addition forms according to the prior art of a compound according to Formula (I) have the disadvantage that their physicochemical stability was found to be poor. Upon storage or formulation of said knows salts, progressive decomposition and concomitantly an increase in the amount and number of impurities was observed. Obviously, this problem is further aggravated under demanding environmental conditions such as light, heat, humidity, acidity, basicity and oxygen. WO99/19317 and WO97/38991 are silent about the stability of the compounds disclosed therein and about ways to obtain or improve stability all together.

Unexpectedly, it has now been found that the above mentioned problem can be solved by using the mandelate salt of the compounds according to Formula (I), the N-oxide forms and the stereochemically isomeric forms thereof. The mandelate salt is not light-sensitive and is far more stable than the prior art salts at room temperature, enhanced temperature and at relative high humidities and in aqueous media.

SUMMARY OF THE INVENTION

The compounds of the present invention can be represented generally by Formula (II)

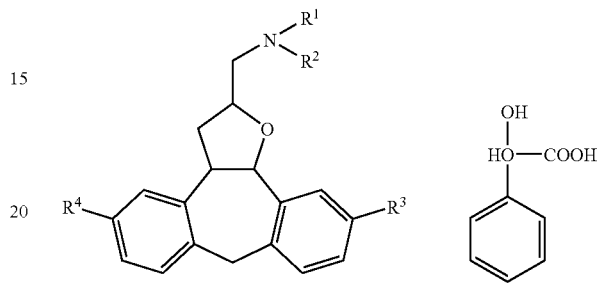

the N-oxide forms and the stereochemically isomeric forms thereof, wherein $R^1$ and $R^2$ each independently are hydrogen or $C_{1-6}$alkyl and $R^3$ and $R^4$ each independently are hydrogen or halogen. In the foregoing definitions $C_{1-6}$alkyl defines straight and branched saturated hydrocarbon radicals having from 1 to 6 carbon atoms such as, for example, methyl, ethyl, propyl, butyl, 1-methylpropyl, 1,1-dimethylethyl, pentyl and hexyl.

BRIEF DESCRIPTION OF THE FIGURES

FIG. 1 provides the absorption/description behavior of various salts of compound X, A=citrate; B=malonate; C=succinate; D=tartrate; E=ditobuoylthatrate; and F=mandelate).

DETAILED DESCRIPTION OF THE INVENTION

In the foregoing definitions halo is generic to fluoro, chloro, bromo and iodo.

Preferred compounds are compounds in which $R^1$ and $R^2$ each independently are hydrogen or methyl.

Preferred compounds are compounds in which $R^3$ and $R^4$ each independently are hydrogen or fluor.

In particular are preferred the compounds in which:

$R^1$ is hydrogen, $R^2$ is methyl, $R^3$ is fluor and $R^4$ is hydrogen (mandelate salt of 11-fluoro-3,3a,8,12b-tetrahydro-N-methyl-2H-dibenzo-[3,4:6,7]cyclohepta[1,2-b]furan-2 methanamine);

$R^1$ is hydrogen, $R^2$ is methyl, $R^3$ is hydrogen and $R^4$ is hydrogen (mandelate salt of 3,3a,8,12b-tetrahydro-N-methyl-2H-dibenzo-[3,4:6,7]cyclohepta[1,2-b]furan-2 methanamine);

$R^1$ is methyl, $R^2$ is methyl, $R^3$ is fluor and $R^4$ is fluor (mandelate salt of 5,11-difluoro-3,3a,8,12b-tetrahydro-N,N-dimethyl-2H-dibenzo-[3,4:6,7]cyclohepta[1,2-b]furan-2 methanamine);

$R^1$ is methyl, $R^2$ is methyl, $R^3$ is fluor and $R^4$ is hydrogen (mandelate salt of 11-fluoro-3,3a,8,12b-tetrahydro-N,N-dimethyl-2H-dibenzo-[3,4:6,7]cyclohepta[1,2-b]furan-2 methanamine);

R¹ is methyl, R² is methyl, R³ is hydrogen and R⁴ is hydrogen (mandelate salt of 3,3a,8,12b-tetrahydro-N, N-dimethyl-2H-dibenzo-[3,4:6,7]cyclohepta[1,2-b]furan-2 methanamine).

The N-oxide forms of the compounds according to Formula (I) and (II) are meant to comprise those compounds of Formula (I) wherein the nitrogen atom is oxidized to the so-called N-oxide.

The term "stereochemically isomeric forms" as used herein defines all possible isomeric forms, which the compounds of Formula (I) and (II) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of Formula (I) and (II) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

Of some compounds of Formula (I) and (II) and of intermediates used in their preparation, the absolute stereochemical configuration was not experimentally determined. In those cases the stereochemically isomeric form which was first isolated is designated as "A" and the second as "B", without further reference to the actual stereochemical configuration. However, said "A" and "B" isomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction.

For example, a compound having the stereochemical descriptor A-(2α,3aβ,12bα) denotes the pure enantiomer having either (a) the [2R-(2α,3aβ,12bα)] configuration whereby carbon atom 2 is the reference atom having the R configuration and the —CH₂—NR¹R² substituent is on the α-side of the mean plane, carbon atom 3a has the S configuration because the hydrogen substituent is on the other side of the mean plane relative to the —CH₂—NR¹R² substituent, and carbon atom 12b has the R configuration because the hydrogen substituent is on the same side of the mean plane relative to the —CH₂—NR¹R² substituent, or (b) the [2S-(2α,3aβ,12bα)] configuration whereby carbon atom 2 has the S configuration, carbon atom 3a the R configuration and carbon atom 12b the S configuration.

Similarly, a compound having the stereochemical descriptor A-(2α,3aα,12bβ) denotes the pure enantiomer having either (a) the [2R-(2α,3aα,12bβ)] configuration whereby carbon atom 2 is the reference atom having the R configuration and the —CH₂—NR¹R² substituent is on the α-side of the mean plane, carbon atom 3a has the R configuration and carbon atom 12b has the S configuration, or (b) the [2S-(2α,3aα,12bβ)] configuration whereby carbon atom 2 has the S configuration, carbon atom 3a the S configuration and carbon atom 12b the R configuration.

We note that the furan-moiety in Formula (I) comprises three stereogenic carbon atoms, respectively at positions 2, 3a and 12b. Therefor, Formula (I) comprises 8 different isomers. Most particularly preferred are the isomers denoted as (2α, 3aα, 12bβ).

Since mandelic acid exists in two isomeric forms (the R and S-form), it is understood that salts of both isomeric forms, including any mixture thereof, are embraced by the scope of this invention. Particularly preferred is the S-form of the mandelate salt.

The compounds of the present invention show affinity for 5-HT$_2$ receptors, particularly for 5-HT$_{2A}$ and 5-HT$_{2C}$ receptors (nomenclature as described by D. Hoyer in "Serotonine (5-HT) in neurologic and psychiatric disorders" edited by M. D. Ferrari and published in 1994 by the Boerhaave Commission of the University of Leiden). The serotonine antagonistic properties of the present compounds may be demonstrated by their inhibitory effect in the "5-hydroxytryptophan Test on Rats" which is described in Drug Dev. Res., 13, 237-244 (1988). Furthermore, the mandelate salts according to the present invention show interesting pharmacological activity in the "mCPP Test on Rats" which is described in WO99/19317, and in the "Combined Apomorphine, Tryptamine, Norepinephrine (ATN) Test on Rats" which is described in Arch. Int. Pharmacodyn., 227, 238-253 (1977).

The present invention thus also relates to mandelate salts according to the invention as defined above for use as a medicine, in particular, the compounds of Formula (II) may be used for the manufacture of a medicament for treating CNS disorders, such as anxiety, psychosis, schizophrenia, depression, migraine, sleep disorders and addictive properties of drugs of abuse.

In particular, the mandelate salts according to the invention are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders.

In particular, the mandelate salts according to the invention may also be used as anxiolytics, antipsychotics, antidepressants, anti-migraine agents and as agents having the potential to overrule the addictive properties of drugs of abuse.

The mandelate salts according to the invention may also be used as therapeutic agents in the treatment of motoric disorders. It may be advantageous to use the mandelate salts according to the invention in combination with classical therapeutic agents for such disorders.

The mandelate salts according to the invention may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the mandelate salts according to the invention, it follows that the present invention also provides a method of treating warm-blooded animals suffering from such diseases, said method comprising the systemic administration of a therapeutic amount of a compound of Formula (II), an N-oxide form or stereochemically isomeric form thereof, effective in treating the above described disorders, in particular, in treating anxiety, psychosis, schizophrenia, depression, migraine, sleep disorders and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

For ease of administration, the subject compounds may be formulated into various pharmaceutical forms for administration purposes. To prepare the pharmaceutical compositions of this invention, a therapeutically effective amount of the particular compound as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing the mandelate salts according to the invention may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. The mandelate salts, being an acid addition salts of compounds of Formula (I) due to their increased water solubility over the corresponding base or acid form, are more suitable in the preparation of aqueous compositions.

In order to enhance the solubility and/or the stability of the compounds of Formula (II) in pharmaceutical compositions, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin. Also co-solvents such as alcohols may improve the solubility and/or the stability of the compounds of Formula (II) in pharmaceutical compositions.

Other convenient ways to enhance the solubility of the compounds of the present invention in pharmaceutical compositions are described in WO 97/44014.

More in particular, the present compounds may be formulated in a pharmaceutical composition comprising a therapeutically effective amount of particles consisting of a solid dispersion comprising (a) a compound of Formula (II), and
(b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions, which are less homogenous throughout than solid solutions. Such dispersions are not chemically and physically uniform throughout or comprise more than one phase.

The water-soluble polymer in the particles is a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The mandelate salts according to Formula (II) can generally be prepared by dissolving the free base of the compounds according to Formula (I) in a suitable solvent, optionally heating the mixture, adding a sufficient quantity of the mandelic acid, cooling the reaction mixture and collecting the crystalline material. The thus obtained corresponding salts may be further refined by recrystallization in a suitable solvent.

The term suitable solvent as used herein in relation to the preparation of the mandelate salts and the recrystallization defines any lower alkanol or ketone solvent in which the compound according to Formula (I) is soluble and includes primary, secondary and tertiary alcohols and the corresponding ketones of from 1 to 6 carbon atoms. Suitable lower alkanol solvents include methanol, ethanol, 1-propanol, 2-propanol, 1-butanol, 2-butanol, 2-methyl-1-propanol, 1,1-dimethyl-ethanol, cyclohexanol and the like. Mixtures of two or more of the above mentioned solvents may also effectively be employed in the preparation of the mandelate salts according to the invention, as well as solutions of said solvents or mixtures thereof with water. In particular, the water may comprise up to about 25% to 35% by volume of said solution. Preferably the solvent used is a lower alkanol, particularly 2-propanol.

The compounds according to Formula (I) may be prepared according to procedures described in WO99/19317 and WO97/38991 and those procedures are disclosed herein by reference.

Generally, the compounds of Formula (I) can be prepared by N-alkylating an intermediate of Formula (III) with an intermediate of Formula (IV) wherein W is a suitable leaving group such as halo. In the intermediates (III) and (IV), $R^1$ to $R^4$ are as defined in the compounds of Formula (I). Said N-alkylation can conveniently be carried out in a reaction-inert solvent such as, for example, methanol, tetrahydrofuran, methylisobutyl ketone, N,N-dimethylformamide or dimethylsulfoxide, and optionally in the presence of a suitable base. Stirring and elevated temperatures, for instance reflux temperature, may enhance the rate of the reaction. Alternatively, said N-alkylation may also be performed using the procedure described by Monkovic et al. (J. Med. Chem. (1973), 16(4), p. 403-407) which involves the use of a pressurized reaction vessel.

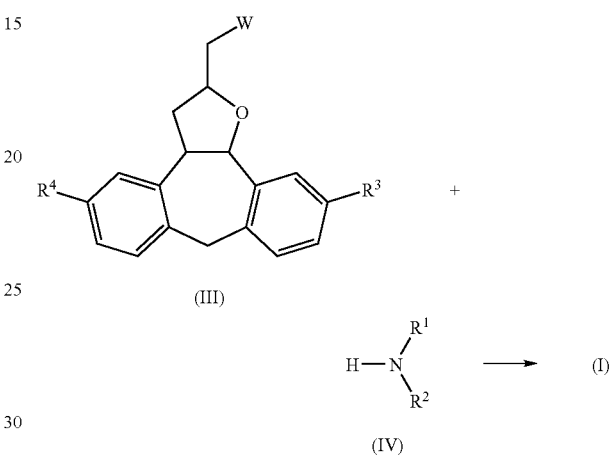

The compounds of Formula (I) may also be converted into each other following art-known transformation reactions.

In addition, the compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of Formula (I) may be obtained by the application of art-known procedures. Diastereomers may be separated by physical methods such as selective crystallization and chromatographic techniques, e.g. counter-current distribution, liquid chromatography and the like.

The compounds of Formula (I) as prepared in the hereinabove described processes are generally racemic mixtures of enantiomers, which can be separated from one another following art-known resolution procedures. The racemic compounds of Formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The intermediates mentioned hereinabove are either commercially available or may be made following art-known procedures. For instance, intermediates of Formula (III) may be prepared according to the procedure described by Monkovic et al. (J. Med. Chem. (1973), 16(4), p. 403-407).

The following examples are intended to illustrate and not to limit the scope of the present invention.

Experimental

A. Preparation of the Intermediate Compounds a) LiAlH$_4$ (0.0686 mol) was added dropwise to a suspension of AlCl$_3$ (0.0718 mol) in tetrahydrofuran (75 ml), cooled on an ice-bath and under N$_2$ atmosphere. The mixture was stirred for 10 minutes at 0° C. A solution of 2-fluoro-5H-dibenzo[a,d]cyclohepten-5-one (0.0653 mol and prepared as described in DE 3,644,462) in tetrahydrofuran (75 ml) was added dropwise and the resulting reaction mixture was allowed to warm to room temperature. Then, the reaction mixture was stirred and refluxed for 2 hours. The mixture was cooled on an ice-bath. Water and CH$_2$Cl$_2$ was added. The organic layer was washed with a saturated aqueous NaHCO$_3$ solution, dried, filtered and the solvent was evaporated, yielding 13.16 g (96%) of 2-fluoro-5H-dibenzo[a,d]cycloheptene (intermediate 1)

b) Metachloroperbenzoic acid (0.0501 mol) was dissolved in CHCl$_3$ (40 ml). The organic solution was dried, filtered and the filtrate was added dropwise to a solution of intermediate 1 (0.0417 mol) and 1,4-benzenediol (0.26 g) in CHCl$_3$ (70 ml), stirred at 60° C. The reaction mixture was stirred for 2.5 hours at 60° C., then cooled on an ice-bath, washed with a 10% aqueous Na$_2$CO$_3$ solution and brine, dried, filtered and the filtrate was evaporated, yielding 10.42 g of 3-fluoro-6,10b-dihydro-1aH-dibenzo-[3,4:6,7]cyclohept[1,2-b]oxirene (intermediate 2)

c) Bromo-2-propenyl-magnesium (0.0542 mol) was added dropwise to a solution of intermediate 2 (0.04956 mol) in tetrahydrofuran (120 ml) under N$_2$ atmosphere. The reaction mixture was stirred for 30 minutes at room temperature, then stirred and refluxed for 2 hours. The reaction mixture was cooled on an ice-bath, quenched with a 20% NH$_4$Cl solution, and extracted with ethyl acetate. The organic layer was separated, dried, filtered and the solvent was evaporated. The residue was purified and separated into two regio-isomers by HPLC over silica gel (eluent: hexanes/ethyl acetate 9/1). Two pure fraction groups were collected and their solvent was evaporated, yielding 4.79 g (36%) of (±)-trans-8-fluoro-10,11-dihydro-11-(2-propenyl)-5H-dibenzo[a,d]cyclo-hepten-10-ol (intermediate 3) and 2.52 g (19%) of (trans)-2-fluoro-10,11-dihydro-11-(2-propenyl)-5H-dibenzo[a,d]cyclohepten-10-ol (intermediate 4).

d) Pyridinium tribromide (0.0175 mol) was added portion wise to a solution of intermediate 3 (0.0175 mol) in CHCl$_3$ (80 ml), cooled on an ice-bath. The reaction mixture was stirred for one hour at room temperature. Water was added. The mixture was stirred for 5 min. The organic layer was separated, washed with water, dried, filtered and the solvent was evaporated. The residue was purified by short column chromatography over silica gel (eluent: hexanes/CH$_2$Cl$_2$ 4:1, then 1:1). The pure fractions were collected and the solvent was evaporated, yielding 5.02 g (83%) of (±)-[(2α,3αβ,12bα)+(2α,3αα,12bβ)]-2-(bromomethyl)-11-fluoro-3,3a,8,12b-tetrahydro-2H-dibenzo-[3,4:6,7]-cyclohepta[1,2-b]furan (intermediate 5).

In a similar way is prepared:

(±)-[(2α,3αβ,12bα)+(2α,3αα,12bβ)]-2-(bromomethyl)-5-fluoro-3,3a,8,12b-tetrahydro-2H-dibenzo-[3,4:6,7]-cyclohepta[1,2-b]furan (intermediate 6), (±)-[(2α,3αβ,12bα)+(2α,3αα,12bβ)]-2-(bromomethyl)-3,3a,8,12b -tetrahydro-2H-dibenzo-[3,4:6,7]-cyclohepta[1,2-b]furan (intermediate 7) and (±)-[(2α,3αβ,12bα)+(2α,3αα,12bβ)]-2-(bromomethyl)-5,11-difluoro-3,3a,8,12b-tetrahydro-2H-dibenzo[3,4:6,7]cyclohepta[1,2-b]furan (intermediate 8).

e) A mixture of intermediate 5 (0.073 mol), dimethylamino gas (170 g) and CaO (26 g) in THF (400 ml) was heated for 16 hours at 125° C. (autoclave) (reaction×2). The mixture was washed with a saturated aqueous NaHCO$_3$ solution, then extracted with CH$_2$Cl$_2$. The separated organic layer was dried, filtered and the solvent evaporated. The residue was dissolved in diethyl ether and converted into the hydrochloric acid salt (1:1) with HCl/2-propanol (pH<4). The solvent was evaporated. The residue was stirred in boiling 2-propanone, filtered off and dried. Yielding: 20.5 g of (±)-(2α,3αβ,12bα)-11-fluoro-3,3a,8,12b-tetrahydro-N,N-dimethyl-2H-dibenzo[3,4:6,7]cyclohepta[1,2-b]furan-2-methanamine (intermediate 9).

f) The solvent of the mother liquor was evaporated. The residue was purified by high-performance liquid chromatography over RP-18 (eluent: (0.5% NH4OAc in H$_2$O)/CH$_3$OH/CH$_3$CN gradient elution). The pure fractions were collected and the solvent was evaporated. Yielding: 0.400 g of (±)-(2α,3αα,12bβ)-11-fluoro-3,3a,8,12b -tetrahydro-N,N-dimethyl-2H-dibenzo[3,4:6,7]cyclohepta[1,2-b]furan-2-methanamine (intermediate 10).

g) Intermediate 10 (0.00128 mol) was separated into its enantiomers by chiral column chromatography over Chiralpak AD (eluent: hexane/2-propanol 97/3). Two pure fraction groups were collected and their solvent was evaporated. Yielding: 0.201 g of A-(2α,3αα,12bβ)-11-fluoro-3,3a,8,12b-tetrahydro-N,N-dimethyl-2H-dibenzo[3,4:6,7]cyclohepta[1,2-b]furan-2-methanamine (intermediate 11) and 0.170 g of B-(2α,3αα,12bβ)-11-fluoro-3,3a,8,12b-tetrahydro-N,N-dimethyl-2H-dibenzo[3,4:6,7]cyclohepta[1,2-b]furan-2-methanamine (intermediate 12).

Analogous to intermediate 10, the following intermediates were also prepared:

(±)-(2α,3aα,12bβ)-5-fluoro-3,3a,8,12b-tetrahydro-N,N-dimethyl-2H-dibenzo[3,4:6,7]cyclohepta[1,2-b]furan-2-methanamine (intermediate 13), (±)-(2α,3aα,12bβ)-3,3a,8,12b-tetrahydro-N,N-dimethyl-2H-dibenzo[3,4:6,7]cyclohepta[1,2-b]furan-2-methanamine (intermediate 14) and (±)-(2α,3aα,12bβ)-5,11-difluoro-3,3a,8,12b-tetrahydro-N,N-dimethyl-2H-dibenzo[3,4:6,7]cyclohepta[1,2-b]furan-2-methanamine (intermediate 15).

d) Using methylamine (gas) instead of N,N-dimethylamine (gas), in a similar way are prepared the monomethyl equivalents of intermediates 13, 14 and 15, yielding (±)-(2α,3aα,12bβ)-11-fluoro-3,3a,8,12b-tetrahydro-N-methyl-2H-dibenzo[3,4:6,7]cyclohepta[1,2-b]furan-2-methanamine (intermediate 16), (±)-(2α,3aα,12bβ)-5-fluoro-3,3a,8,12b-tetrahydro-N-methyl-2H-dibenzo[3,4:6,7]cyclohepta[1,2-b]furan-2-methanamine (intermediate 17), (±)-(2α,3aα,12bβ)-5,11-difluoro-3,3a,8,12b-tetrahydro-N-methyl-2H-dibenzo[3,4:6,7]cyclohepta[1,2-b]furan-2-methanamine (intermediate 18) and (±)-(2α,3aα,12bβ)-3,3a,8,12b-tetrahydro-N-methyl-2H-dibenzo[3,4:6,7]cyclohepta[1,2-b]furan-2-methanamine (intermediate 19).

B. Preparation of the Mandelate Salts

Compound 1

0.00025 mol of the B-enantiomer of intermediate 16 and 0.00025 mol of S-mandelic acid were dissolved in 4 ml of 2-propanol, then allowed to crystallize. The precipitate was filtered off and dried (vacuum, 50° C.). Yield: 0.096 g of mandelate salt (Compound 1). 5 mg of Compound 1 was recrystallised from 1 ml of 2-propanol, including 3 drops of ethanol in order to obtain a sample, suitable for X-ray analysis.

In a similar way were prepared the mandelate salts of the B-enantiomers of intermediates 12, 13, 14, 15, 17, 18 and 19.

Stability Testing

The following salts were tested: tartrate salt, ditoluoyltartrate salt, citrate salt, malonate salt, succinate salt and mandelate salt (Compound 1) of B-(2α,3aα,12bβ)-11-fluoro-3,3a,8,12b-tetrahydro-N-methyl-2H-dibenzo-[3,4:6,7]cyclohepta[1,2-b]furan-2 methanamine. The salts were tested for their water adsorption/desorption behaviour, their crystallographic stability and their chemical stability.

a. Adsorption and Desorption of Water

The adsorption and desorption of water at 25° C. at different conditions of relative humidity is investigated on an amount of ±10 mg of each salt. The weight change as a function of relative humidity is registered. The results are displayed in FIG. 1. The mandelate salt is stable towards moisture uptake over the whole range of humidity. The malonate salt, succinate salt, tartrate salt, and the (+)ditoluoyltartrate salt are less stable but the weight change as a function of the relative humidity is very small. The citrate salt is hygroscopic and liquefies at high relative humidity.

b. Crystallographic Stability.

The stability of the crystal structure of the salt is studied after storage of the compounds for a period of two weeks at room temperature (RT) under either 5%, 75% and 25° C./60% relative humidity (RH). The samples are analyzed with thermogravimetry (TGA), differential scanning calorimetry (DSC) and infrared spectroscopy (IR).

The results of the tests are reported in Table 1.

TABLE 1

Results for the crystallographic stability.

| Salt | Condition | TGA <100° C. | IR | DSC Max (° C.) | DSC ΔH (J/g) | Appearance |
|---|---|---|---|---|---|---|
| Tartrate | 0 days | 0.0 | Ref | 158.8 | 85.9 | white |
| | RT/<5% RH | 0.0 | ~Ref | 160.3 | 86.4 | white |
| | RT/56% RH | 0.1 | ~Ref | 159.0 | 86.2 | white |
| | RT/75% RH | 0.0 | ~Ref | 159.0 | 85.5 | white |
| Mandelate | 0 days | 0.1 | Ref | 229.5 | 141.1 | white |
| | RT/<5% RH | 0.1 | ~Ref | 229.1 | 140.2 | white |
| | 25° C./60% RH | 0.1 | ~Ref | 229.1 | 139.0 | white |
| | RT/75% RH | 0.1 | ~Ref | 229.4 | 137.6 | white |
| Citrate | 0 days | (*) | Ref | amorphous | | yellowish |
| | RT/75% RH | (*) | (*) | (*) | | liquefied |
| (+)ditoluoyltartrate | 0 days | 0.2 | Ref | 173.7 | 71.9 | white |
| | RT/<5% RH | 0.3 | ~Ref | 175.6 | 78.7 | white |
| | 25° C./60% RH | 0.1 | ~Ref | 177.6 | 74.7 | white |
| | RT/75% RH | 0.2 | ~Ref | 178.6 | 70.8 | white |

\* No measurements performed
~Ref: identical with reference

No change is observed for the tartrate salt, the mandelic acid salt and the (+)ditoluoyltartrate salt during storage under the different relative humidities. The IR spectra and the DSC curves remain the same before and after storage. This indicates that the products are crystallographic stable. The citrate salt is amorphous and liquefies at RT/75% RH.

c. Chemical Stability

In the chemical stability test program the salts are stored for periods of 2, 4 and 8 weeks under different conditions. These conditions are 40° C./75% RH, 50° C., daylight, RT/5% RH, RT/75% RH, 25° C./60% RH and artificial light. The mandelate salt and the ditoluoyltartrate salt are also stored 8 hours in 0.3 da ICH light. The compounds are analyzed after storage by HPLC and by visual inspection.

The results of the tests are reported in Table 2.

TABLE 2

Results for the chemical stability.

| Salt | Condition | HPLC Sum of impurities | | | Appearance | | |
|---|---|---|---|---|---|---|---|
| | | 2 weeks | 4 weeks | 8 weeks | 2 weeks | 4 weeks | 8 weeks |
| Tartrate | Reference | 0.72 | — | — | white | — | — |
| | Artificial light | 0.79 | — | — | white | — | — |
| | 40° C./75% RH | 0.72 | 0.83 | 0.93 | white | white | almost white |
| | 50° C. | 0.72 | 0.77 | 0.79 | white | white | almost white |
| | Daylight | 0.75 | 0.85 | 0.91 | white | almost white | slightly yellow |
| | RT/<5% RH | — | 0.73 | 0.75 | — | white | white |
| | 25° C./60% RH | — | 0.75 | 0.77 | — | white | white |
| | RT/75% RH | — | 0.72 | 0.80 | — | white | white |
| Mandelate | Reference | 1.72 | — | — | white | — | — |
| | Artificial light | 1.70 | — | — | white | — | — |
| | 0.3 da ICH light | 1.70 | — | — | white | — | — |
| | 40° C./75% RH | 1.73 | 1.73 | 1.70 | white | white | white |
| | 50° C. | 1.74 | 1.75 | 1.70 | white | white | white |
| | Daylight | 1.73 | 1.71 | 1.72 | white | white | white |
| | RT/<5% RH | — | 1.73 | 1.72 | — | white | white |
| | 25° C./60% RH | — | 1.71 | 1.69 | — | white | white |
| | RT/75% RH | — | 1.75 | 1.76 | — | white | white |
| Citrate | Reference | 4.76 | — | — | yellow | — | — |
| | Artificial light | 8.99 | — | — | ochre-yellow | — | — |
| | 40° C./75% RH | 4.83 | 7.91 | 10.62 | liquefied | liquefied | liquefied |
| | 50° C. | 6.29 | 7.47 | 9.07 | ochre-yellow | ochre-yellow | orange-brown |
| | Daylight | 5.81 | 5.99 | 6.31 | ochre-yellow | ochre-yellow | orange-brown |
| | RT/75% RH | — | 4.69 | 4.98 | — | liquefied | liquefied |
| (+)ditoluoyltartrate | Reference | 1.01 | — | — | white | — | — |
| | Artificial light | 1.57 | — | — | white | — | — |
| | 0.3 da ICH light | 1.41 | — | — | white | — | — |
| | 40° C./75% RH | 0.98 | 1.00 | 1.09 | white | white | white |
| | 50° C. | 1.06 | 1.22 | 1.25 | white | white | white |
| | Daylight | 1.26 | 1.65 | 1.74 | white | white | white-yellow |

The chemical stability study of the different forms resulted in following observations:

The tartrate salt showed a sensitivity towards 40° C./70% RH and light, as the sum of impurities increases after storage at 40° C./70% RH and in the two light conditions. The citrate salt shows degradation in all investigated conditions.

The (+)ditoluoyltartrate salt shows a sensitivity towards temperature and light, as the sum of impurities increases after storage at 50° C. and in the two light conditions. The mandelate salt is chemically stable in all investigated conditions.

In summary, the tartrate salt shows a good adsorption desorption profile, is crystallographically stable but shows sensitivity towards higher humidities and light. The citrate salt is hygroscopic and liquefies at high relative humidity during the adsorption desorption test. The citrate salt is amorphous and chemically not stable. It is sensitive to degradation in all storage conditions. The (+)ditoluoyltartrate salt, shows a good adsorption desorption profile, is crystallographically stable but shows sensitivity towards temperature and light. On the other hand, the mandelate salt shows a good adsorption/desorption profile and is crystallographically and chemically stable.

It was also found that the stability of the salts increased with increasing purity. Also, the prior art salts were difficult to prepare with a high degree of purity while the mandelate salt could always be prepared with a high degree of purity. Therefore, the mandelate salt is the better choice when it comes down to choosing salts with a sufficient stability.

The invention claimed is:

1. A mandelate salt of a compound according to Formula (I),

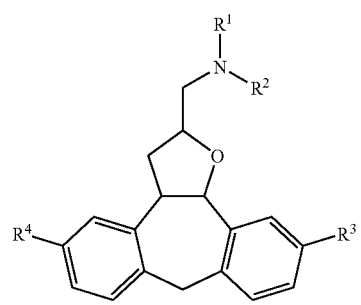

the N-oxide forms and the (2α,3aα,12bβ)-isomeric forms thereof, wherein $R^1$ and $R^2$ each independently are hydrogen or $C_{1-6}$alkyl, $R^3$ and $R^4$ each independently are hydrogen or halogen, $C_{1-6}$alkyl defines straight and branched saturated hydrocarbon radicals having from 1 to 6 carbon atoms and halo is generic to fluoro, chloro, bromo and iodo.

2. A mandelate salt according to claim 1, wherein $R^1$ and $R^2$ each independently are hydrogen or methyl.

3. A mandelate salt according to claim 1, wherein $R^3$ and $R^4$ each independently are hydrogen or fluor.

4. A mandelate salt according to claim 1, wherein the compound is the mandelate salt of:
- 11-fluoro-3,3a,8,12b-tetrahydro-N-methyl-2H-dibenzo-[3,4:6,7]cyclohepta-[1,2-b]furan-2 methanamine;
- 3,3a,8,12b-tetrahydro-N-methyl-2H-dibenzo-[3,4:6,7]cyclohepta [1,2-b]furan-2 methanamine;
- 5,11-difluoro-3,3a,8,12b-tetrahydro-N,N-dimethyl-2H-dibenzo-[3,4:6,7]cyclohepta [1,2-b]furan-2 methanamine;
- 11-fluoro-3,3a,8,12b-tetrahydro-N,N-dimethyl-2H-dibenzo-[3,4:6,7]cyclohepta [1,2-b]furan-2 methanamine or
- 3,3a,8,1 2b-tetrahydro-N,N-dimethyl-2H-dibenzo-[3,4:6,7]cyclohepta [1,2-b]furan-2 methanamine.

5. A mandelate salt according to claim 1, wherein the mandelate salt has the S-form.

6. A mandelate salt according to claim 1, for use as a medicine.

7. A pharmaceutical composition comprising a pharmaceutically acceptable carrier and as active ingredient, a therapeutically effective amount of a mandelate salt according to claim 1.

8. A process for preparing a mandelate salt according to claim 1, characterized in dissolving the free base of a compound according to Formula (I) in a suitable solvent, optionally heating the mixture, adding a sufficient quantity of the mandelic acid, cooling the reaction mixture and collecting the crystalline material, optionally further refining the mandelate salt by recrystallization in a suitable solvent.

9. The S-mandelate salt according to claim 1 of B-[(2α,3aα,12bβ)]11-fluoro-3,3a,8,12b-tetrahydro-N-methyl-2H-dibenzo-[3,4:6,7]cyclohepta-[1,2-b]furan-2 methanamine.

* * * * *